(12) United States Patent
Fuchs et al.

(10) Patent No.: US 8,349,224 B2
(45) Date of Patent: Jan. 8, 2013

(54) MELAMINE PHENYLPHOSPHONATE FLAME RETARDANT COMPOSITIONS

(75) Inventors: Sabine Fuchs, Mannheim (DE); Thomas Weiβ, Ilvesheim (DE); Rainer Xalter, Basel (CH)

(73) Assignee: BASF SE Ludwigshafen (DE)

( * ) Notice: Subject to any disclaimer, the term of this patent is extended or adjusted under 35 U.S.C. 154(b) by 0 days.

(21) Appl. No.: 13/131,904

(22) PCT Filed: Nov. 25, 2009

(86) PCT No.: PCT/EP2009/065804
§ 371 (c)(1),
(2), (4) Date: Jul. 19, 2011

(87) PCT Pub. No.: WO2010/063623
PCT Pub. Date: Jun. 10, 2010

(65) Prior Publication Data
US 2011/0266507 A1    Nov. 3, 2011

(30) Foreign Application Priority Data
Dec. 4, 2008  (EP) .................... 08170642

(51) Int. Cl.
*C09K 21/00* (2006.01)
*C09K 21/10* (2006.01)
*C09K 21/12* (2006.01)

(52) U.S. Cl. ........... 252/609; 252/601; 523/451; 558/82
(58) Field of Classification Search ................ 252/609, 252/601
See application file for complete search history.

(56) References Cited

U.S. PATENT DOCUMENTS
4,061,605 A   12/1977 Simon

FOREIGN PATENT DOCUMENTS
JP    2001049087 A  *  2/2001

OTHER PUBLICATIONS

Database WPI Week 200413 Thomson Scientific, AN 2004-125330, Abst_JP 2001 049087, 2001.
Database WPI Week 200940 Thomson Scientific, AN 2009-K39252, Abst_JP 2001 342357, 2001.

* cited by examiner

*Primary Examiner* — Peter F Godenschwager
(74) *Attorney, Agent, or Firm* — Tyler A. Stevenson

(57) ABSTRACT

The present invention relates to flame retardant polymer compositions which comprise melamine phenylphosphonates and mixtures with dihydro-oxa-phosphaphenanthrene derivatives. The compositions are especially useful for the manufacture of flame retardant compounds based on polyfunctional epoxides or polycondensates like polyesters, polyamides and polycarbonates.

4 Claims, No Drawings

MELAMINE PHENYLPHOSPHONATE FLAME RETARDANT COMPOSITIONS

The present invention relates to flame retardant polymer compositions which comprise melamine phenylphosphonates and mixtures of melamine phenylphosphonates with dihydro-oxa-phosphaphenanthrene derivatives. The compositions are especially useful for the manufacture of flame retardant compounds based on polyfunctional epoxides or polycondensates like polyesters, polyamides and polycarbonates.

Flame retardants are added to polymeric materials (synthetic or natural) to enhance the flame retardant properties of the polymers. Depending on their composition, flame retardants may act in the solid, liquid or gas phase either chemically, e.g. as a spumescent by liberation of nitrogen, and/or physically, e.g. by producing a foam coverage. Flame retardants interfere during a particular stage of the combustion process, e.g. during heating, decomposition, ignition or flame spread.

There is still a need for flame retardant compositions with improved properties that can be used in different polymer substrates. Increased standards with regard to safety and environmental requirements result in stricter regulations. Particularly known halogen containing flame retardants no longer match all necessary requirements. Therefore, halogen free flame retardants are preferred, particularly in view of their better performance in terms of smoke density associated with fire. Improved thermal stability and less corrosive behaviour are further benefits of halogen free flame retardant compositions.

It has surprisingly been found that polymers with excellent flame retardant properties are prepared in the event that melamine phosphonate salts are added to the polymer substrate. By use of the flame retardant compositions according to the invention halogen containing flame retardants, such as tetrabromobisphenol (TBBA) and antimony compounds, may be largely reduced or replaced.

The invention relates to a composition, particularly a flame retardant composition, which comprises
a) A melamine phenylphosphonate salt of the formula

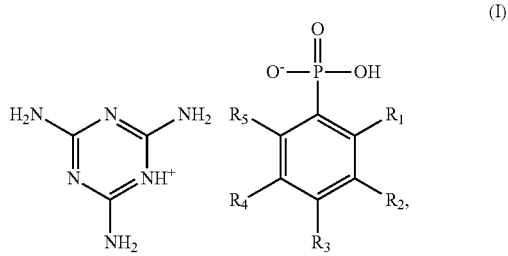

(I)

Wherein
$R_1$-$R_5$ independently of one another represent hydrogen or a substituent selected from the group consisting of $C_1$-$C_4$alkyl, hydroxy, hydroxy-$C_1$-$C_4$alkyl and $C_1$-$C_4$alkoxy; and
b) A polymer substrate.

In the melamine phenylphosphinate salt (I) defined above, the molar ratio of the phenylphosphinic acid and the melamine base are present is about 0.8-1.2:1.0, preferably about 0.9-1.1:1.0, particularly about 1.0:1.0 (equimolar amounts of the phenylphosphinic acid and the melamine base).

The composition defined above for use as a flame retardant is another embodiment of the invention.

A preferred embodiment of the invention relates to a composition, particularly a flame retardant composition, which comprises a) A melamine phenylphosphonate salt (I), wherein
$R_1$-$R_5$ represent hydrogen; or
1-3 of $R_1$-$R_5$ represent a substituent selected from the group consisting of $C_1$-$C_4$alkyl, hydroxy-$C_1$-$C_4$alkyl and $C_1$-$C_4$alkoxy; and the other ones represent hydrogen; and
b) A polymer substrate.

A more preferred embodiment of the invention relates to a composition, particularly a flame retardant composition, which comprises
a) The melamine phenylphosphonate salt of the formula

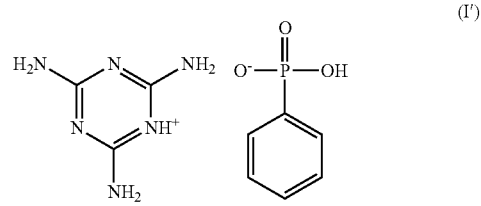 [SMILES: Nc1nc(N)[nH+]c(N)n1 ; O=P([O-])(O)c1ccccc1]

(I')

and
b) A polymer substrate.

A specific embodiment of the invention relates to a composition, which comprises
a) A melamine phenylphosphonate salt (I), wherein
$R_1$-$R_5$ independently of one another represent hydrogen or a substituent selected from the group consisting of $C_1$-$C_4$alkyl, hydroxy, hydroxy-$C_1$-$C_4$alkyl and $C_1$-$C_4$alkoxy; and
b) A polymer substrate selected from the group consisting of polyfunctional epoxide compounds, hardener compounds and thermoplastic polymers.

A more specific embodiment of the invention relates to a composition, particularly a flame retardant composition, which comprises
a) The melamine phenylphosphonate salt of the formula

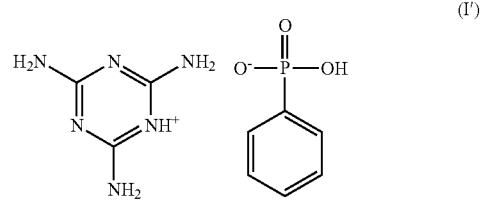 [SMILES: Nc1nc(N)[nH+]c(N)n1 ; O=P([O-])(O)c1ccccc1]

(I')

and
b) A polymer substrate selected from the group consisting of polyfunctional epoxide compounds and hardener compounds.

A preferred embodiment relates to a composition, which comprises
a) A melamine phenylphosphonate salt of the formula

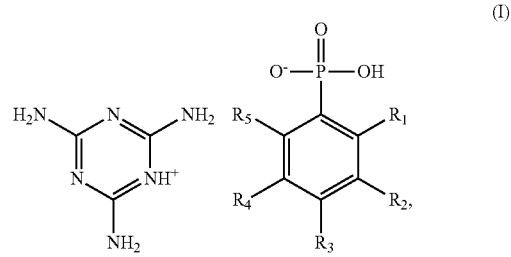

(I)

Wherein
$R_1$-$R_5$ independently of one another represent hydrogen or a substituent selected from the group consisting of $C_1$-$C_4$alkyl, hydroxy, hydroxy-$C_1$-$C_4$alkyl and $C_1$-$C_4$alkoxy;

In combination with oxaphosphorinoxide or a derivative thereof, as represented by the formula

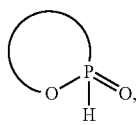

(II)

and
b) A polymer substrate selected from the group consisting of polyfunctional epoxide compounds and hardener compounds.

A particularly preferred embodiment relates to a composition, which comprises
a) A melamine phenylphosphonate salt (I), wherein
$R_1$-$R_5$ represent hydrogen; or
1-3 of $R_1$-$R_5$ represent a substituent selected from the group consisting of $C_1$-$C_4$alkyl, hydroxy-$C_1$-$C_4$alkyl and $C_1$-$C_4$alkoxy; and the other ones represent hydrogen; and
b) A polymer substrate selected from the group consisting of polyfunctional epoxide compounds and hardener compounds.

A highly preferred embodiment relates to a composition, which comprises
a) The melamine phenylphosphonate salt of the formula

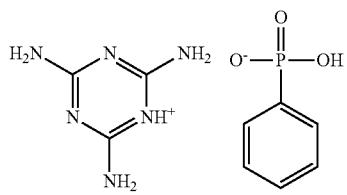

(I')

In combination with oxaphosphorinoxide or a derivative thereof, as represented by the formula

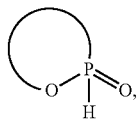

(II)

and
b) A polymer substrate selected from the group consisting of polyfunctional epoxide compounds and hardener compounds.

A highly desirable embodiment relates to a composition, which comprises
a) The melamine phenylphosphonate salt of the formula (I') in combination with R-substituted oxaphosphorinoxides of the formula

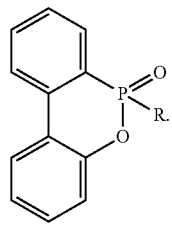

(IIb)

Wherein the phenyl groups may be substituted by additional substituents and R represents $C_1$-$C_{18}$alkyl or $C_6$-$C_{12}$ aryl, which may be substituted by further substituents; and b) A polymer substrate selected from the group consisting of polyfunctional epoxide compounds and hardener compounds.

A highly preferred embodiment of the invention relates to a composition, particularly a flame retardant composition, which comprises
a) The melamine phenylphosphonate salt of the formula

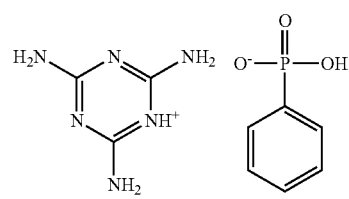

(I')

In combination with 6H-dibenz[c,e][1,2]oxazaphosphorin-6-oxide of the formula:

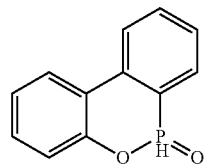

(II)

or a derivative thereof; and
b) A polymer substrate selected from the group consisting of polyfunctional epoxide compounds and hardener compounds.

The compositions according to the invention attain the desirable V-0 rating, according to UL-94 (Underwriter's Laboratories Subject 94) and other excellent ratings in related test methods, especially in glass fibre reinforced formulations where conventional FR systems tend to fail.

The composition, as defined above, comprises the following components:

Component a)
In a melamine phenylphosphonate salt of the formula

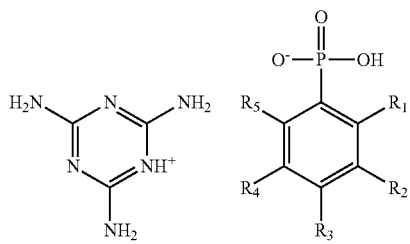

(I)

$R_1$-$R_5$ independently of one another represent hydrogen or a substituent selected from the group consisting of $C_1$-$C_4$alkyl, e.g. methyl, ethyl, n- or isopropyl, or n-, iso- or tert-butyl, hydroxy, hydroxy-$C_1$-$C_4$alkyl, e.g. hydroxymethyl or 1- or 2-hydroxyethyl and $C_1$-$C_4$alkoxy, e.g. methoxy or ethoxy.

In the melamine phenylphosphinate salt (I) defined above, the molar ratio of the phenylphosphinic acid and the melamine base are present is about 0.8-1.2:1.0, preferably about 0.9-1.1:1.0, particularly about 1.0:1.0 (equimolar amounts of the phenylphosphinic acid and the melamine base).

The melamine phenylphosphonate salt (I) as defined above is obtainable by known methods, e.g. acid-base reaction of equivalent amounts of melamine with phenylphosphonic acid of the formula

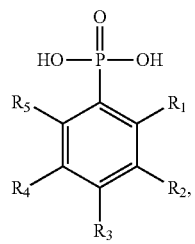

Wherein $R_1$-$R_5$ are as defined above.

According to a preferred embodiment, melamine phenylphosphonate is prepared from melamine and phenylphosphonic acid, for example by addition of both components as hot aqueous solutions, followed by subsequent crystallization, filtration, drying and milling.

A further embodiment of the invention relates to the melamine phenylphosphonate salt (I) component of the formula

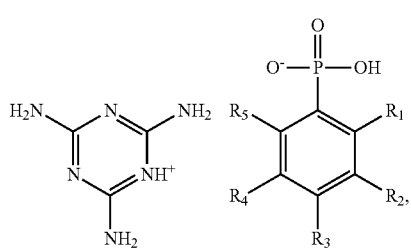

(I)

Wherein $R_1$-$R_5$ independently of one another represent hydrogen or a substituent selected from the group consisting of $C_1$-$C_4$alkyl, hydroxy, hydroxy-$C_1$-$C_4$alkyl and $C_1$-$C_4$alkoxy, particularly a melamine phenylphosphonate salt (I), wherein
$R_1$-$R_5$ represent hydrogen; or
1-3 of $R_1$-$R_5$ represent a substituent selected from the group consisting of $C_1$-$C_4$alkyl, hydroxy-$C_1$-$C_4$alkyl and $C_1$-$C_4$alkoxy; and the other ones represent hydrogen.

According to a preferred embodiment, melamine and $R_1$-$R_5$-phenylphosphonic acid are present in the melamine phenylphosphonate acid addition salt of the formula (I) in equimolar amounts.

The invention also relates to the melamine phenylphosphonate salt (I) component of the formula

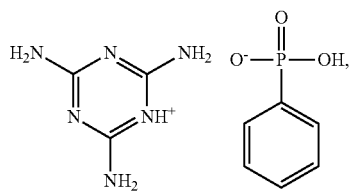

(I')

particularly the 1:1 acid addition salt of the melamine phenylphosphonate salt (I).

According to a preferred embodiment, melamine and phenylphosphinic acidi are present in the melamine phenylphosphonate acid addition salt of the formula (I') in equimolar amounts.

The method for preparing the melamine phenylphosphonate salt (I) is also subject matter of the invention.

According to a preferred embodiment, the melamine phenylphosphonate salt (I) is combined in the flame retardant compositions of the invention with oxaphosphorinoxide or a derivative thereof, as represented by the formula

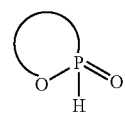

(II)

In the oxaphosphorinoxide (II) the phosphorous atom and one oxygen atom are part of a cyclic structure, particularly a five or six membered ring, and at least one group of the partial formula

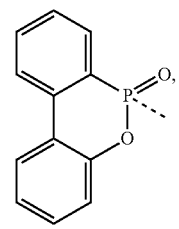

(A)

is present.

According to a preferred embodiment, the oxaphosphorinoxide (II) is represented by the following structural formula:

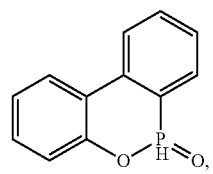

(IIa)

which can be named as 6H-dibenz[c,e][1,2]oxaphosphorin-6-oxide, 3,4:5,6-dibenzo-2H-1,2-oxaphosphorin-2-oxide or 9,10-dihydro-9-oxa-10-phosphorylphenanthrene-10-oxide, abbreviated as DOPO(C.A. RN 35948-25-5). Such compound is commercially available from Sanko Co, Ltd. under the trade name Sanko-HCA.

Two different structural formulae may be assigned to DOPO and its hydrolysis product:

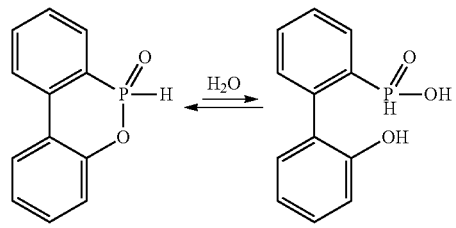

Suitable derivatives of oxaphosphorinoxide are 9,10-dihydro-9-oxa-10-phosphorylphenanthrene-10-oxide (DOPO), salts of DOPO, such as the zinc salts

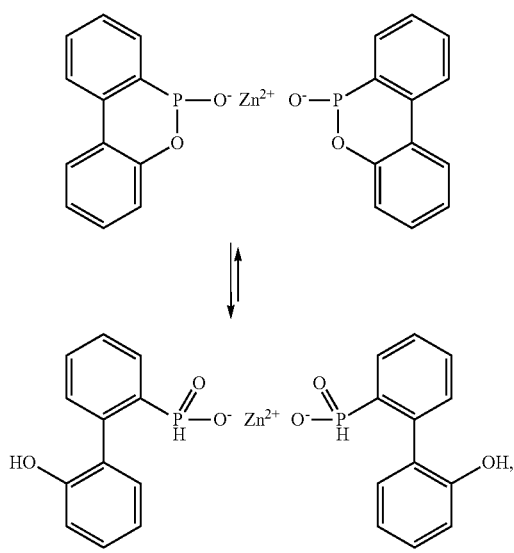

or
R-substituted oxaphosphorinoxides of the formula

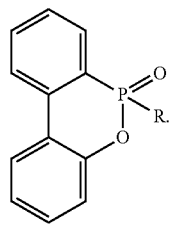
(IIb)

Wherein the phenyl groups may be substituted by additional substituents and R represents $C_1$-$C_{18}$alkyl or $C_6$-$C_{12}$ aryl, which may be substituted by further substituents.

Representative compounds (IIb) are compounds of the formula:

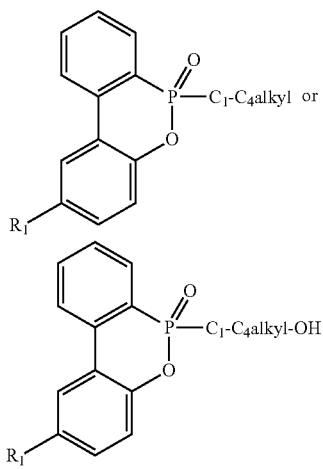

Wherein $R_1$ represents hydrogen or $C_1$-$C_4$alkyl;

Other representative compounds (IIb) are compounds, wherein R represents carboxyalkyl, carboxyalkyl which is esterified by hydroxyalkyl, or represents carboxyimidoalkyl, such as the compounds of the formulae:

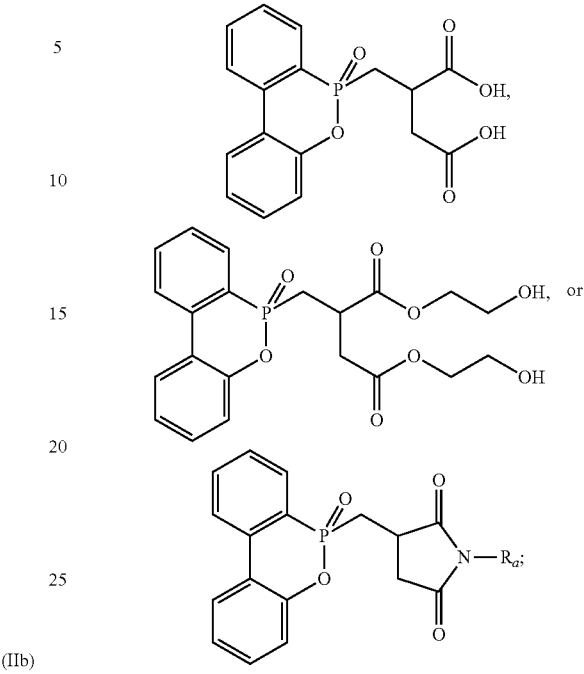

Wherein $R_a$ represents hydrogen or $C_1$-$C_4$alkyl; or represents alkoxyalkyl, such as the compounds of the formula:

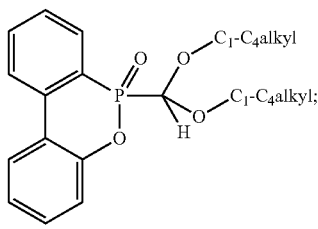

Aryl, such as the compounds of the formulae:

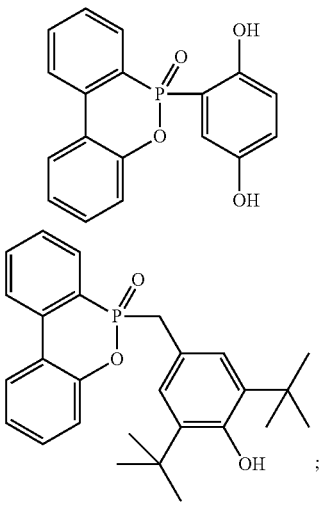

Or wherein R represents arylalkyl, such the compounds of the formulae

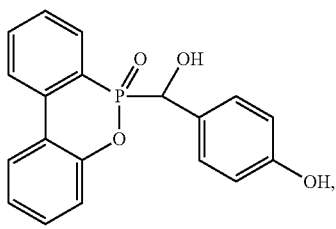

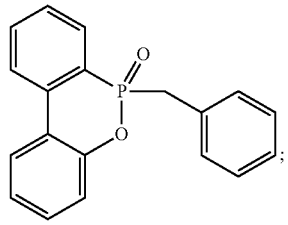

Or wherein R represents alkoxyalkyl substituted by hydroxy, such as the compound of the formula

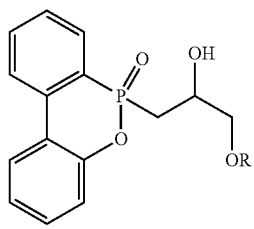

as obtained by reaction of DOPO with epoxides:

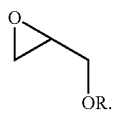

According to an alternative embodiment, suitable derivatives of oxaphosphorinoxide are characterized by the presence of two groups of the partial formula

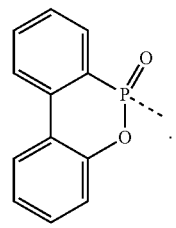

(A)

These groups are connected with a bivalent bridge group X, such as compounds of the formula

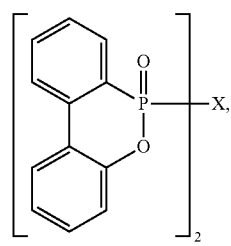

(IIc)

Wherein the phenyl groups may be substituted by further substituents.

Representative examples of these compounds are compounds of the formulae:

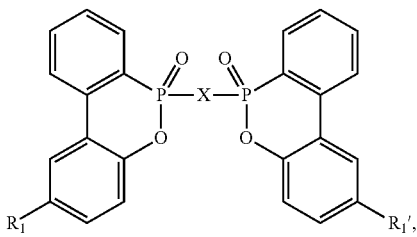

Wherein X represents $C_2$-$C_6$alkylene and $R_1$ and $R_1'$ represent hydrogen or $C_1$-$C_4$alkyl;

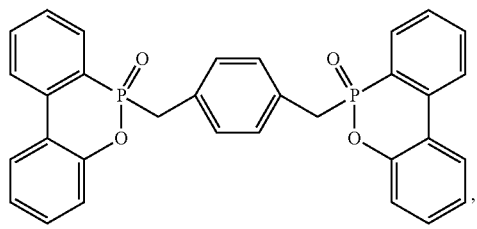

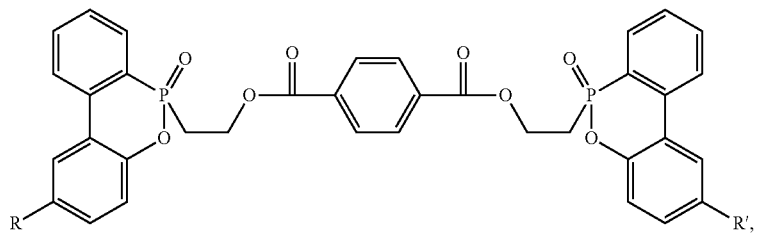

Wherein R and R' represent hydrogen or $C_1$-$C_4$alkyl;

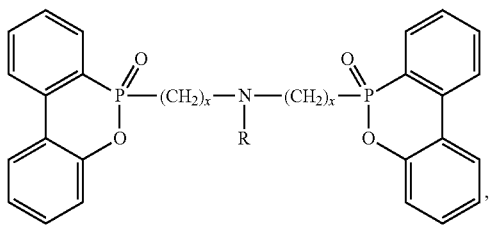

Wherein x represents a numeral from 2 to 4 and R represents $C_1$-$C_4$alkyl or $C_6$-$C_{10}$ aryl or tosyl;

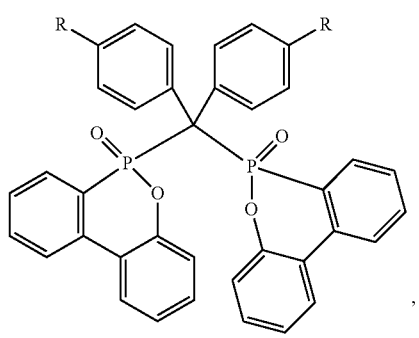

Wherein R represents hydroxy or amino;

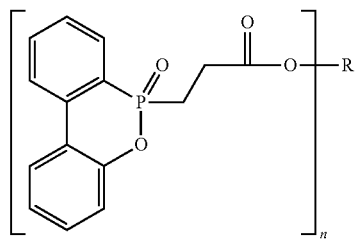

Wherein n represents a numeral from two to six and R represents the ester group from a polyhydroxy alcohol, such as di-, tri- or tetrahydroxy alcohol, e.g. ethylene glycol, trimethylol propane, pentaerythritol or dipentaerythritol, as obtained by reaction of DOPO with acrylic acid-R-esters and subsequent transesterification:

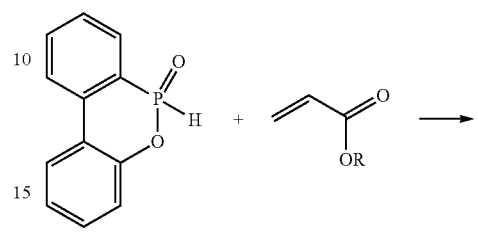

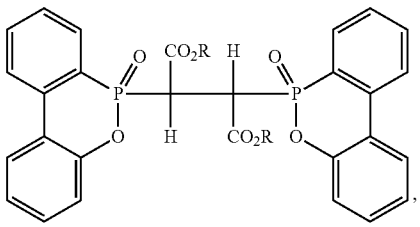

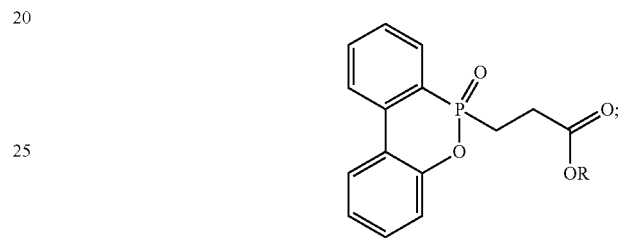

Wherein R represents $C_1$-$C_4$alkyl, as obtained by reaction of:

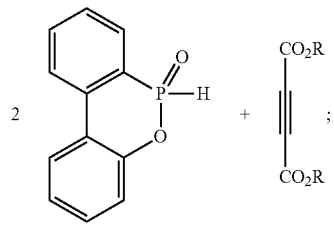

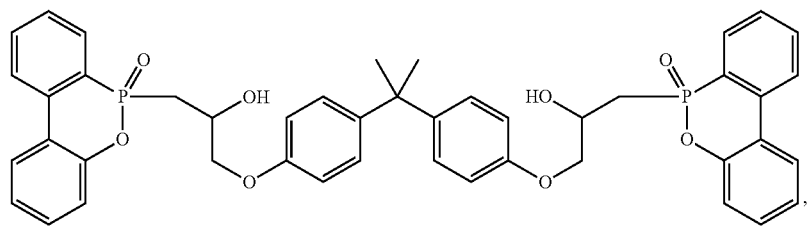

as obtained by the reaction of DOPO with

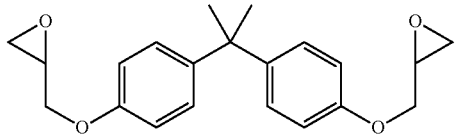 [SMILES: CC(C)(c1ccc(OCC2CO2)cc1)c1ccc(OCC2CO2)cc1]

or the corresponding diacyl derivative thereof of the formula

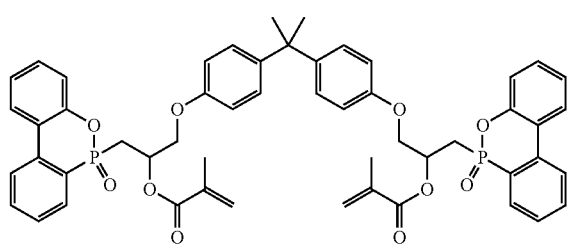 [SMILES: C=C(C)C(=O)OC(COc1ccc(C(C)(C)c2ccc(OCC(CP3(=O)Oc4ccccc4-c4ccccc43)OC(=O)C(=C)C)cc2)cc1)CP1(=O)Oc2ccccc2-c2ccccc21]

Or the compounds of the formulae

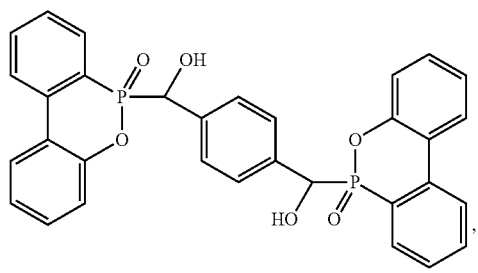

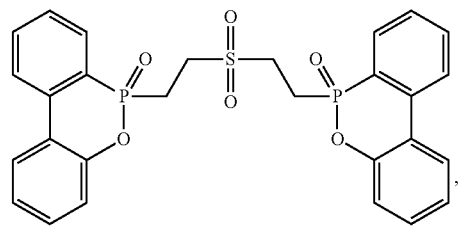

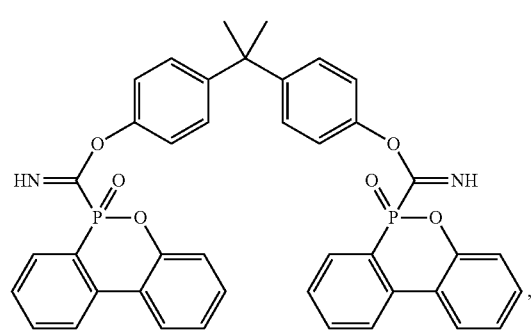

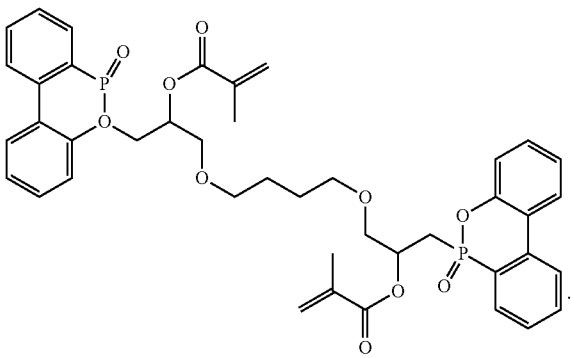

According to an alternative embodiment, suitable derivatives of oxaphosphorinoxide are characterized by the presence of three groups of the partial formula (A). These groups are connected with a trivalent group Y, such as compounds of the formula

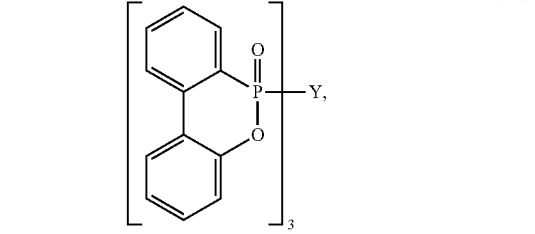 (IId)

Wherein the phenyl groups may be substituted by further substituents.

Representative examples of these compounds are compounds of the formulae:

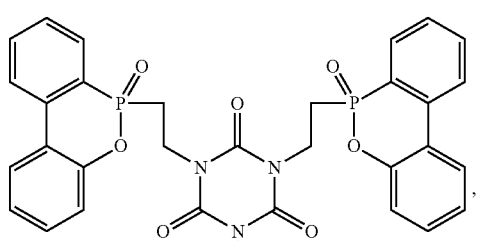

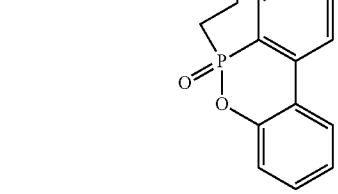

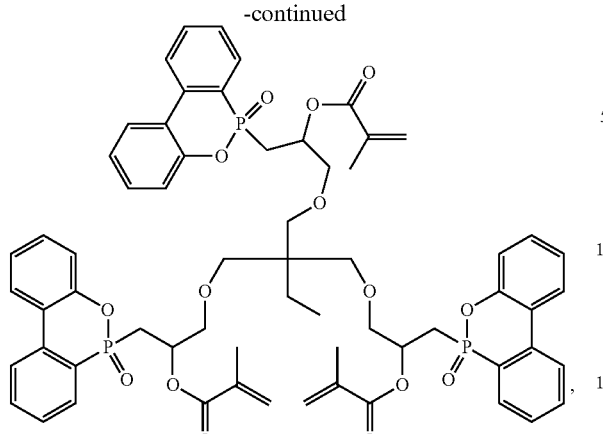

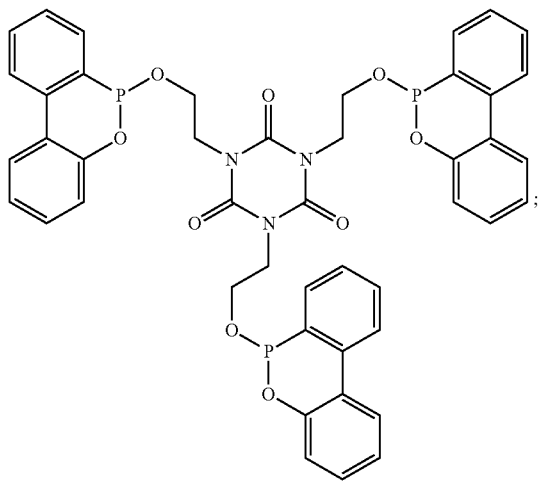

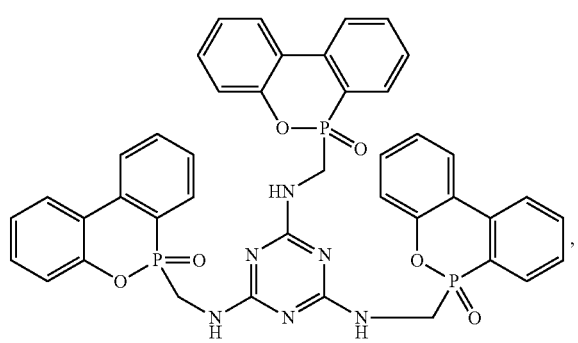

obtainable by condensation of melamine with DOPO and formaldehyde; or

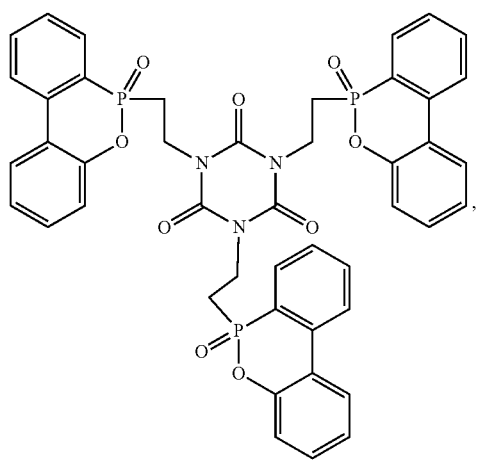 [SMILES: O=c1n(CCP2(=O)Oc3ccccc3-c3ccccc32)c(=O)n(CCP2(=O)Oc3ccccc3-c3ccccc32)c(=O)n1CCP1(=O)Oc2ccccc2-c2ccccc21]

as obtained by intramolecular Michaelis-Arbuzov reaction from

According to an alternative embodiment, suitable derivatives of oxaphosphorinoxide are characterized by the presence of more than three groups of the partial formula (A), according to the structural formulae

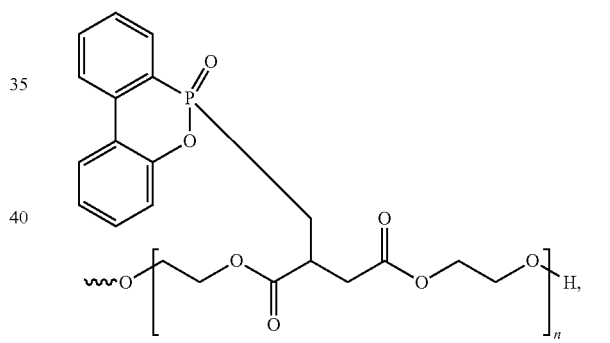

Wherein n represents numerals from 1 to 30, or more preferably from 2 to 10; or

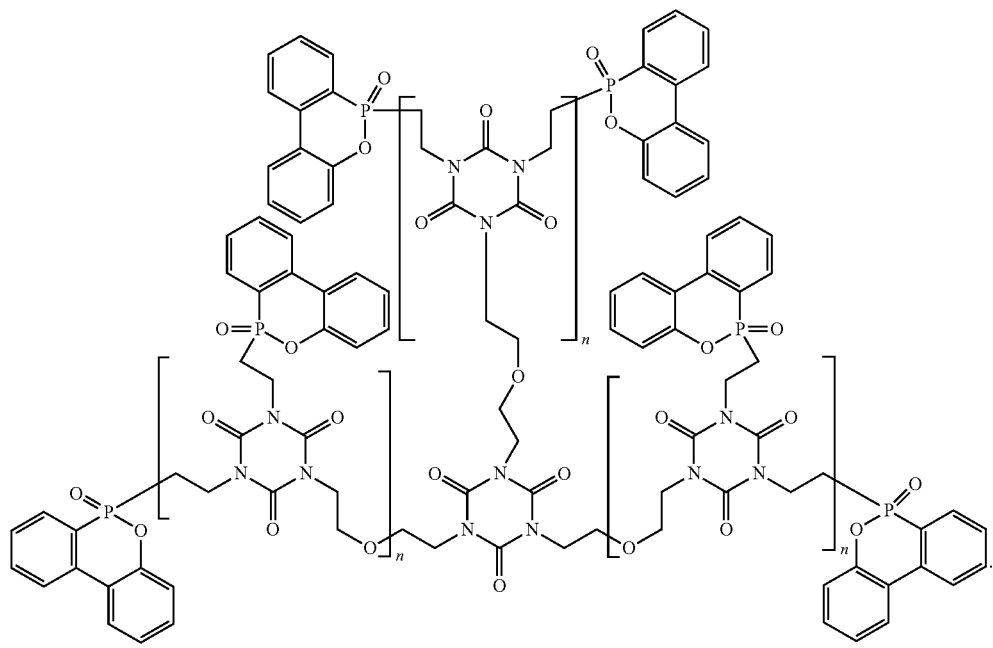

The oxaphosphorinoxides as defined above are known compounds or can be prepared by known methods. Some of them are commercially available.

Component b)

The term polymer substrate comprises within its scope thermoplastic polymers or thermosets.

A list of suitable synthetic polymers is given below:
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be cross linked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE, VLDPE and ULDPE).

Polyolefins, i.e. the polymers of monoolefins exemplified in the preceding paragraph, preferably polyethylene and polypropylene, can be prepared by different and especially by the following methods:
  a) Radical polymerisation (normally under high pressure and at elevated temperature);
  b) Catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, Ia and/or IIIa of the Periodic Table. The activators may be modified conveniently with further ester, ether, and amine or silyl ether groups. These catalyst systems are usually termed Phillips, Standard Oil Indiana, Ziegler-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch;

The homopolymers and copolymers mentioned above may have a stereo structure including syndiotactic, isotactic, hemi-isotactic or atactic; where atactic polymers are preferred. Stereo block polymers are also included.

5. Polystyrene, poly (p-methylstyrene), poly(α-methylstyrene).
6. Aromatic homopolymers and copolymers derived from vinyl aromatic monomers including styrene, α-methylstyrene, all isomers of vinyl toluene, especially p-vinyl toluene, all isomers of ethyl styrene, propyl styrene, vinyl biphenyl, vinyl naphthalene, and vinyl anthracene, and mixtures thereof. Homopolymers and copolymers may have a stereo structure including syndiotactic, isotactic, hemi-isotactic or atactic; where atactic polymers are preferred. Stereo block polymers are also included:
    a) Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene;
    b) Hydrogenated aromatic polymers derived from hydrogenation of polymers mentioned under 6), especially including polycyclohexylethylene (PCHE) prepared by hydrogenating atactic polystyrene, often referred to as polyvinylcyclohexane (PVCH);
    c) Hydrogenated aromatic polymers derived from hydrogenation of polymers mentioned under 6a). Homopolymers and copolymers may have a stereo structure including syndiotactic, isotactic, hemi-isotactic or atactic; where atactic polymers are preferred. Stereo block polymers are also included.
7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.
8. Halogen-containing polymers such as polychloroprene, chlorinated rubbers, chlorinated and brominated copolymer of isobutylene-isoprene (halobutyl rubber), chlorinated or sulphochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.
9. Polymers derived from α,β-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1 above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes, which contain ethylene oxide as a comonomer; polyacetals modified with thermoplastic polyurethanes, acrylates or MBS.
14. Polyphenylene oxides and sulphides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide imides, polyether imides, polyester imides, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.
19. Polyketones.
20. Polysulphones, polyether sulphones and polyether ketones.
21. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

22. Polycarbonates that correspond to the general formula:

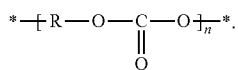

Such Polycarbonates are obtainable by interfacial processes or by melt processes (catalytic transesterification). The polycarbonate may be either branched or linear in structure and may include any functional substituents. Polycarbonate copolymers and polycarbonate blends are also within the scope of the invention. The term polycarbonate should be interpreted as inclusive of copolymers and blends with other thermoplastics. Methods for the manufacture of polycarbonates are known, for example, from U.S. Pat. Nos. 3,030,331; 3,169,121; 4,130,458; 4,263,201; 4,286,083; 4,552,704; 5,210,268; and 5,606,007. A combination of two or more polycarbonates of different molecular weights may be used.

Preferred are polycarbonates obtainable by reaction of a diphenol, such as bisphenol A, with a carbonate source. Examples of suitable diphenols are:

Bisphenol A:

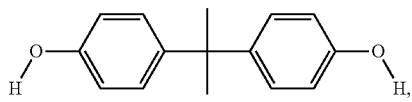

bisphenol AF:

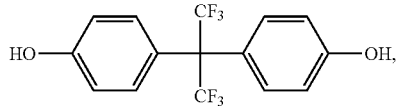

bisphenol AP:

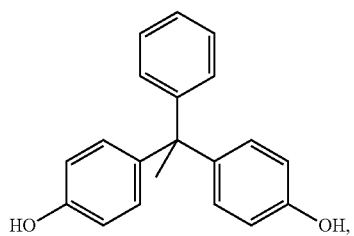

bisphenol B:

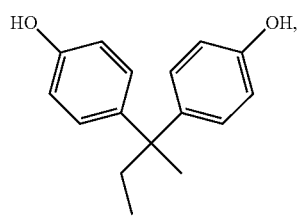

bisphenol C:

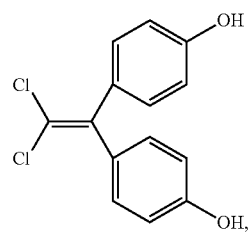

bisphenol E:

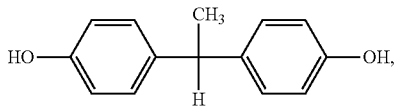

bisphenol F:

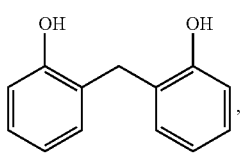

bisphenol M:

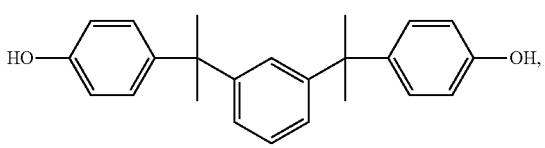

bisphenol P:

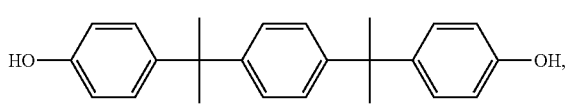

bisphenol S:

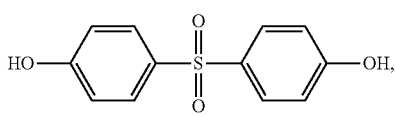

bisphenol TMC:

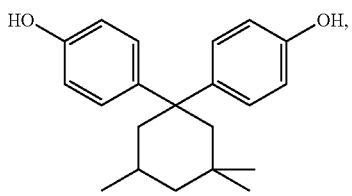

bisphenol Z:

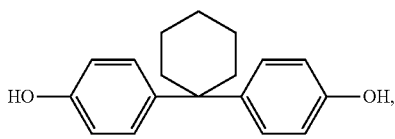

4,4'-(2-norbornylidene)bis(2,6-dichlorophenol); or

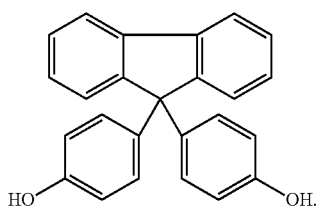

The carbonate source may be a carbonyl halide, a carbonate ester or a haloformate. Suitable carbonate halides are phosgene or carbonylbromide. Suitable carbonate esters are dialkyl-carbonates, such as dimethyl- or diethylcarbonate, diphenyl carbonate, phenyl-alkylphenyl-carbonate, such as phenyl-tolylcarbonate, dialkylcarbonates, such as dimethyl- or diethylcarbonate, di-(halophenyl)carbonates, such as di-(chlorophenyl)carbonate, di-(bromophenyl)carbonate, di- (trichlorophenyl)carbonate or di-(trichlorophenyl)carbonate, di-(alkylphenyl)carbonates, such as di-tolylcarbonate, naphthylcarbonate, dichloronaphthylcarbonate and others.

The polymer substrate mentioned above, which comprises polycarbonates or polycarbonate blends is a polycarbonate-copolymer, wherein isophthalate/terephthalate-resorcinol segments are present. Such polycarbonates are commercially available, e.g. Lexan® SLX (General Electrics Co. USA). Other polymeric substrates of component b) may additionally contain in the form as admixtures or as copolymers a wide variety of synthetic polymers including polyolefins, polystyrenes, polyesters, polyethers, polyamides, poly(meth)acrylates, thermoplastic polyurethanes, polysulphones, polyacetals and PVC, including suitable compatibilizing agents. For example, the polymer substrate may additionally contain thermoplastic polymers selected from the group of resins consisting of polyolefins, thermoplastic polyurethanes, styrene polymers and copolymers thereof. Specific embodiments include polypropylene (PP), polyethylene (PE), polyamide (PA), polybutylene terephthalate (PBT), polyethylene terephthalate (PET), glycol-modified polycyclohexylenemethylene terephthalate (PCTG), polysulphone (PSU), polymethylmethacrylate (PMMA), thermoplastic polyurethane (TPU), acrylonitrile-butadiene-styrene (ABS), acrylonitrile-styrene-acrylic ester (ASA), acrylonitrile-ethylene-propylene-styrene (AES), styrene-maleic anhydride (SMA) or high impact polystyrene (HIPS).

According to a preferred embodiment, the term polymer substrate of component b) consists of a polyfunctional epoxide compound, wherein at least two epoxy groups of the partial formula

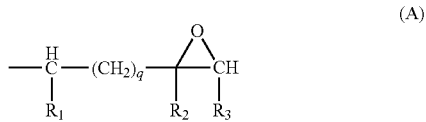

(A)

are present, which are attached directly to carbon, oxygen, nitrogen or sulphur atoms, and wherein q represents zero, $R_1$ and $R_3$ both represent hydrogen and $R_2$ represents hydrogen or methyl; or wherein q represents zero or 1, $R_1$ and $R_3$ together form the —$CH_2$—$CH_2$— or —$CH_2$—$CH_2$—$CH_2$— groups and $R_2$ represents hydrogen.

Examples of polyfunctional epoxide compounds are:
I) Polyglycidyl esters and poly(β-methylglycidyl) esters obtainable by reacting a compound having at least two carboxyl groups in the molecule with epichlorohydrin and/or glyceroldichlorohydrin and/or β-methylepichlorohydrin. The reaction is carried out in the presence of bases.
Suitable compounds having at least two carboxyl groups in the molecule are aliphatic polycarboxylic acids, such as glutaric, adipic, pimelic, suberic, azelaic, sebacic or dimerized or trimerized linoleic acid. Cycloaliphatic polycarboxylic acids are suitable, e.g. tetrahydrophthalic, 4-methyltetrahydrophthalic, hexahydrophthalic or 4-methylhexahydrophthalic acid.
Aromatic polycarboxylic acids are suitable, such as phthalic, isophthalic, trimellitic and pyromellitic acid. Likewise suitable are carboxyl-terminated adducts of, for example, trimellitic acid and polyols such as glycerol or 2,2-bis(4-hydroxycyclohexyl)propane.
II) Polyglycidyl ethers or poly(β-methylglycidyl)ethers obtainable by reacting a compound having at least two free alcoholic hydroxyl groups and/or phenolic hydroxyl groups with a suitably substituted epichlorohydrin under alkaline conditions or in the presence of an acidic catalyst with subsequent treatment under alkaline conditions.

Ethers of this type are derived, for example, from straight-chained alcohols, such as ethyleneglycol, diethyleneglycol and higher poly(oxyethylene) glycols, propane-1,2-diol, or poly(oxypropylene) glycols, propane-1,3-diol, butane-1, 4-diol, poly(oxytetramethylene) glycols, pentane-1,5-diol, hexane-1,6-diol, hexane-2,4,6-triol, glycerol, 1,1,1-trimethylolpropane, bistrimethylolpropane, pentaerythritol, sorbitol, and from polyepichlorohydrins.
In the alternative, they are derived, for example, from cycloaliphatic alcohols, such as 1,3- or 1,4-dihydroxycyclohexane, bis(4-hydroxycyclohexyl)methane, 2,2-bis(4-hydroxycyclohexyl)-propane or 1,1-bis(hydroxymethyl)cyclohex-3-ene, or they possess aromatic nuclei, such as N,N-bis(2-hydroxyethyl)aniline or p,p'-bis(2-hydroxyethylamino)diphenylmethane.
The epoxy compounds may also be derived from mononuclear phenols, such as resorcinol or hydroquinone; or they are based on polynuclear phenols, such as bis(4-hydroxyphenyl)methane, 2,2-bis(4-hydroxyphenyl) propane, 2,2-bis(3,5-dibromo-4-hydroxyphenyl)-propane or 4,4'-dihydroxydiphenyl sulphone, or on condensates of phenols with formaldehyde that are obtained under acidic conditions, such as phenol Novolak®.
III) Poly(N-glycidyl) compounds obtainable by dehydrochlorinating the reaction products of epichlorohydrin with amines containing at least two amino hydrogen atoms. These amines are, for example, aniline, toluidine, n-butylamine, bis(4-aminophenyl)methane, m-xylylenediamine or bis(4-methylaminophenyl)methane, and also N,N,O-triglycidyl-m-aminophenol or N,N,O-triglycidyl-p-aminophenol.
The poly(N-glycidyl) compounds also include N,N'-diglycidyl derivatives of cycloalkylene-ureas, such as ethylene urea or 1,3-propyleneurea, and N,N'-diglycidyl derivatives of hydantoins, such as of 5,5-dimethylhydantoin.
IV) Poly(S-glycidyl) compounds, such as di-S-glycidyl derivatives derived from dithiols, such as ethane-1,2-dithiol or bis(4-mercaptomethylphenyl)ether.

Epoxy compounds having a radical of the formula A, in which $R_1$ and $R_3$ together are —$CH_2$—$CH_2$— and n is 0 are bis(2,3-epoxycyclopentyl)ether, 2,3-epoxycyclopentyl glycidyl ether or 1,2-bis(2,3-epoxycyclopentyloxy)ethane. An example of an epoxy resin having a radical of the formula A in which $R_1$ and $R_3$ together are —$CH_2$—$CH_2$— and n is 1 is (3,4-epoxy-6-methylcyclohexyl)methyl 3',4'-epoxy-6'-methylcyclohexanecarboxylate.

Polyfunctional epoxide compounds are known. Many of them are commercially available from Huntsman Advanced Materials (brand name Araldite®). Examples of suitable polyfunctional epoxides are:
a) Liquid bisphenol A diglycidyl ethers, such as ARALDITE GY 240, GY 250, GY 260, GY 266, GY 2600, MY 790, DER® 332, 331, Hexion® EPR 158, Tactix® 123 and 138, or Epon® 826;
b) Solid bisphenol A diglycidyl ethers such as ARALDITE GT 6071, GT 7071, GT 7072, GT 6063, GT 7203, GT 6064, GT 7304, GT 7004, GT 6084, GT 1999, GT 7077, GT 6097, GT 7097, GT 7008, GT 6099, GT 6608, GT 6609, GT 6610, CT 200 and 6100 ES, Epikote® 1001 and 109, and DER® 661, 667 and 668 and DLS 1065 ES;
c) Liquid bisphenol F diglycidyl ethers, such as ARALDITE GY 281, GY 282, PY 302, and PY 306;
d) Solid polyglycidyl ethers of tetraphenylethane, such as CG Epoxy Resin®0163;
e) Solid and liquid polyglycidyl ethers of phenol-formaldehyde Novolak®, such as EPN 1138, EPN 1139, GY 1180, PY 307, Epon® 828 and Tactix® 556;

f) Solid and liquid polyglycidyl ethers of o-cresol-formaldehyde NOVOLAK, such as ECN 1235, 1273, 1280 and ECN 1299;
g) Liquid glycidyl ethers of alcohols, such as Shell®glycidyl ether 162, ARALDITE DY 0390, and DY 0391;
h) Liquid glycidyl ethers of carboxylic acids, such as Shell®Cardura E terephthalic ester, trimellitic ester, and PY 284;
i) Solid heterocyclic epoxy resins (triglycidyl isocyanurate), such as ARALDITE PT 810;
k) Liquid cycloaliphatic epoxy resins, such as ARALDITE CY 179;
l) Liquid N,N,O-triglycidyl ethers of p-aminophenol, such as ARALDITE MY 0510;
m) Tetraglycidyl-4,4'-methylenebenzamine or N,N,N',N'-tetraglycidyldiaminophenylmethane, such as ARALDITE MY 720, and MY 721;
n) N,N,N',N'-tetraglycidyl-m-xylidenediamine, such as Tetrad®-X;
o) Triglycidyl ether of 1,1,2,-tris(4-hydroxyphenyl)ethane, such as Tactix® 742.

If desired, a mixture of epoxy compounds of different structure can also be employed.

Suitable polyfunctional epoxide compounds preferably comprise at least two groups of the formula

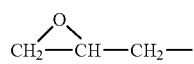

Particular preference as component is given to the following compounds of types and/or mixtures of them

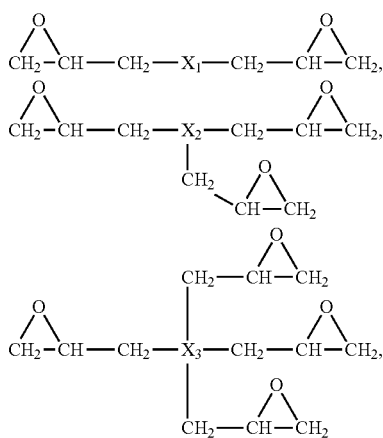

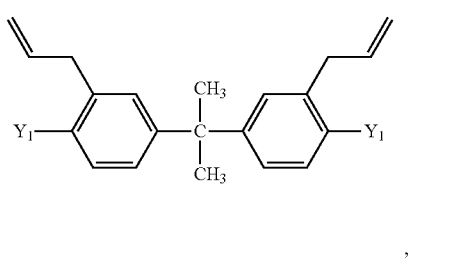

Wherein $X_1$, $X_2$ and $X_3$ are cyclohexylene, phenylene or naphthylene which can be unsubstituted or substituted and $X_1$ is additionally an unsubstituted or substituted radical of the partial formula

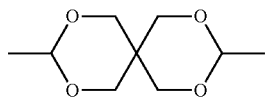

and $X_2$ is additionally an unsubstituted or substituted radical of the partial formula

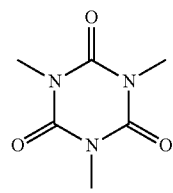

Suitable substituents for the abovementioned radicals are —O—, —S—, —C(=O)—, —C(=O)—O—, —S(=O)—, —S($O_2$)—, —C($CF_3$)$_2$—, alkyl, alkylene, aryl, arylene, alkoxy, aryloxy or halogen. Identical or different substituents may be present two or more times, whereas the substituents themselves may likewise be further substituted.

An example of a suitable alkyl radical is a $C_1$-$C_{18}$ alkyl radical, such as methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl, and their branched isomers.

Possible alkylene and alkoxy radicals can be derived formally from the above-mentioned alkyl radicals by removing a further hydrogen atom or, respectively, by adding an oxygen atom.

Examples of suitable aryl radicals are those having 6-20 carbon atoms, such as phenylene, biphenylene or naphthylene.

Possible arylene and aryloxy radicals can be derived formally from the abovementioned aryl radicals by removing a further hydrogen atom or, respectively, by adding an oxygen atom.

Preference is given to radicals of the following formulae:
for $X_1$:

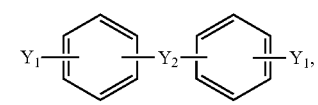

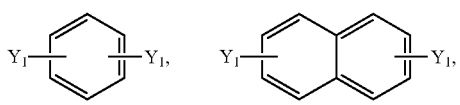

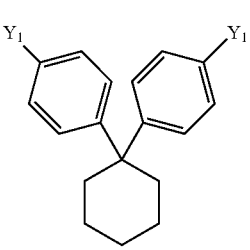

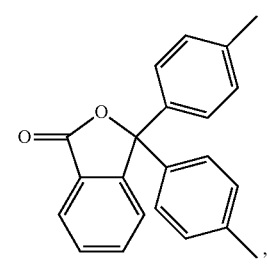

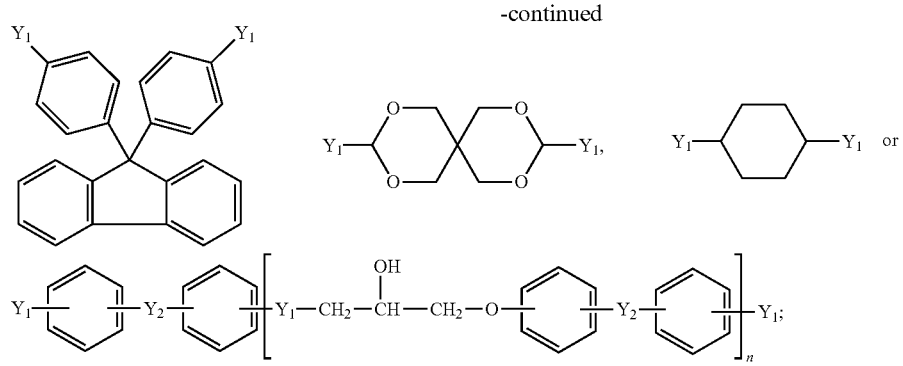
for $X_2$:
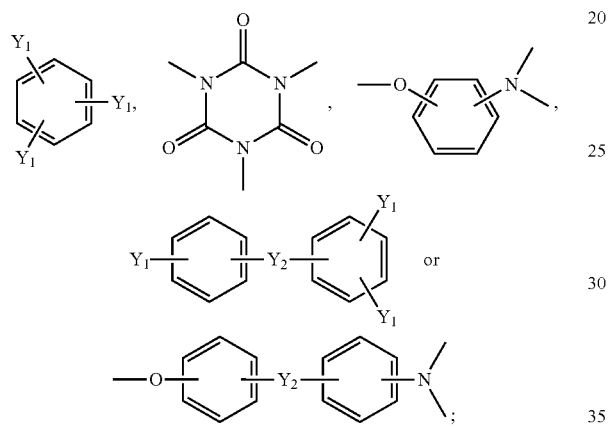
for $X_3$:
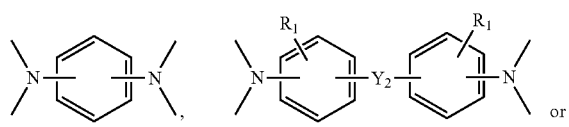
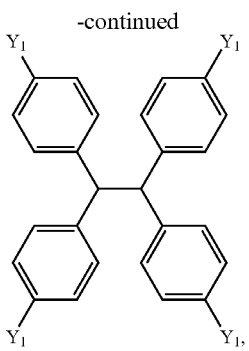
in which
$Y_1$ is a direct bond or the groups —O—, —S— or —C(=O)—O—;
$Y_2$ is a direct bond or the groups —SO$_2$—, —CO—, —S—, —SO—, CH$_2$, —C(CH$_3$)$_2$— or —C(CF$_3$)$_2$—;
And n is 1-10.
The aromatic rings are unsubstituted or substituted one or more times by alkyl, aryl, alkoxy, aryloxy or halogen, as described in more detail above.
Particular preference is given to the following compounds:
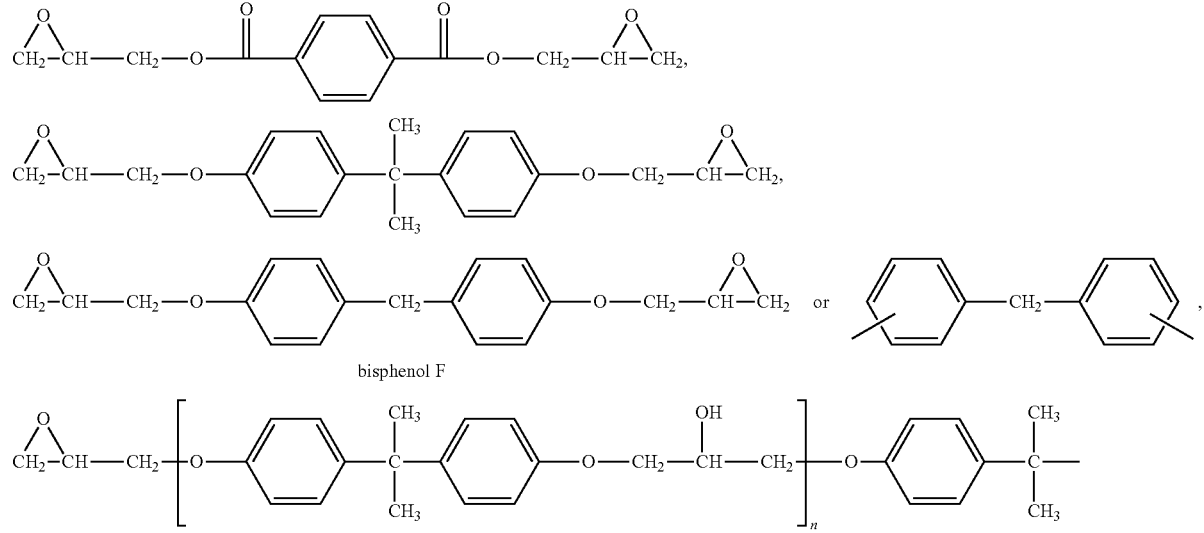

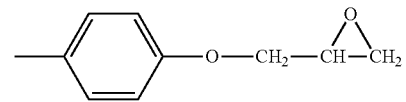

(n = 1-10)

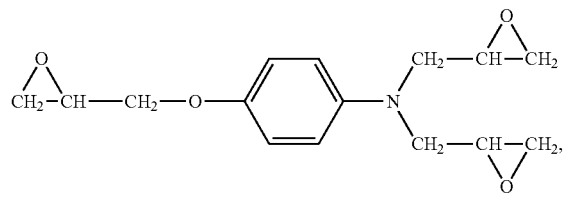

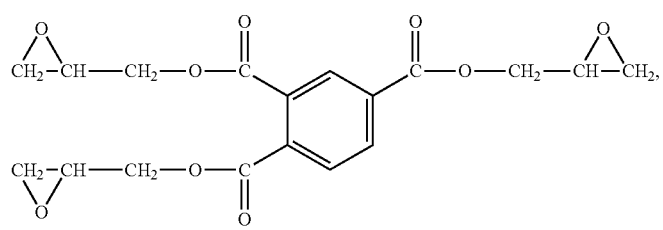

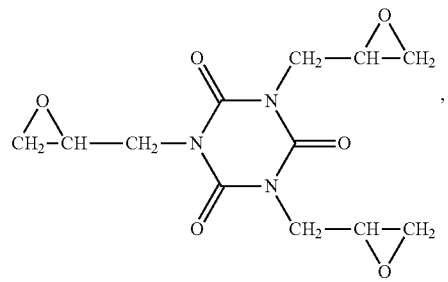

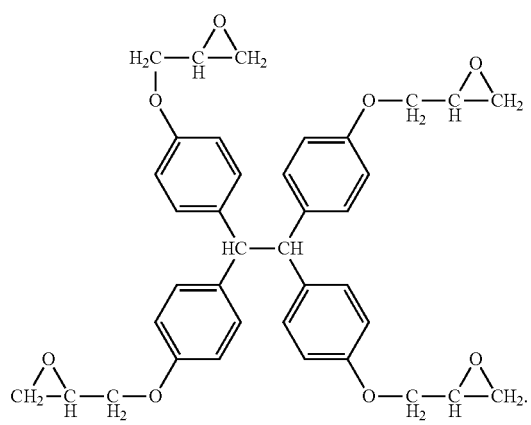

According to a preferred embodiment, a hardener component is present in the composition. A suitable hardener compound is any of the known hardeners for epoxy resins. The amine, phenolic and anhydride hardeners are particularly preferred, such as polyamines, e.g. ethylenediamine, diethylenetriamine, triethylenetriamine, hexamethylenediamine, methanediamine, N-aminoethyl piperazine, diaminodiphenylmethane [DDM], alkyl-substituted derivatives of DDM, isophoronediamine [IPD], diaminodiphenylsulphone [DDS], 4,4'-methylenedianiline [MDA], or m-phenylenediamine [MPDA]), polyamides, alkyl/alkenyl imidazoles, dicyandiamide [DICY], 1,6-hexamethylene-bis-cyanoguanidine, phenolic hardeners such as phenol novolac and cresol novolac, or acid anhydrides, e.g. dodecenylsuccinic acid anhydride, hexahydrophthalic acid anhydride, tetrahydrophthalic acid anhydride, phthalic acid anhydride, pyromellitic acid anhydride, and derivatives thereof.

A preferred embodiment of the invention relates to a composition, which comprises as component b) a polyfunctional epoxide compound a hardener compound that contains at least two amino groups, such as dicyandiamide.

A particularly preferred embodiment of the invention relates to a composition, which comprises a) about 0.05-30.0 wt. % of melamine phenylphosphonate salt (I);

b) about 60.0-95.0 wt % of a polyfunctional epoxide compound; and 0.10-40.0 wt % of a hardener compound.

Additional Components

The instant invention further pertains to a composition, which comprises, in addition to the components a) and b), as defined above, further additives selected from the group consisting of so-called anti-dripping agents, polymer stabilizers and additional flame retardants, such as phosphorus containing flame-retardants, nitrogen containing flame retardants, halogenated flame-retardants and inorganic flame-retardants.

According to a preferred embodiment the invention relates to a composition, which comprises in addition to the melamine phenylphosphonate salt (I) of Component a), optionally combined with oxaphosphorinoxide or derivatives thereof, further additives selected from the group consisting of polymer stabilizers and additional flame retardants.

According to another embodiment, the invention relates to a composition which additionally comprises as additional component so-called anti-dripping agents.

These anti-dripping agents reduce the melt flow of the thermoplastic polymer and inhibit the formation of drops at high temperatures. Various references, such as U.S. Pat. No. 4,263,201, describe the addition of anti-dripping agents to flame retardant compositions.

Suitable additives that inhibit the formation of drops at high temperatures include glass fibers, polytetrafluoroethylene (PTFE), high temperature elastomers, carbon fibers, glass spheres and the like.

The addition of polysiloxanes of different structures has been proposed in various references; cf. U.S. Pat. No. 6,660,787, 6,727,302 or 6,730,720.

Stabilizers are preferably halogen-free and selected from nitroxyl stabilizers, nitrone stabilizers, amine oxide stabilizers, benzofuranone stabilizers, phosphite and phosphonite stabilizers, quinone methide stabilizers and monoacrylate esters of 2,2'-alkylidenebisphenol stabilizers.

According to a preferred embodiment of the invention, the composition comprises an additional flame retardant component. Such additional flame retardants are known components, items of commerce or can be obtained by known methods.

Other representative phosphorus containing flame retardants, in addition to the ones defined above, are for example:

Tetraphenyl resorcinol diphosphate (Fyrolflex® RDP, Akzo Nobel), resorcinol diphosphate oligomer (RDP), tetrakis(hydroxymethyl)phosphonium sulphide, triphenyl phosphate, diethyl-N,N-bis(2-hydroxyethyl)-aminomethyl phosphonate, hydroxyalkyl esters of phosphorus acids, salts of hypophosphoric acid ($H_3PO_2$) formed with e.g. $Ca^{2+}$, $Zn^{2+}$, or $Al^{3+}$ as cations, ammonium polyphosphate (APP) or (Hostaflam® AP750), resorcinol diphosphate oligomer (RDP), phosphazene flame-retardants and ethylenediamine diphosphate (EDAP).

Nitrogen containing flame-retardants are, for example, isocyanurate flame-retardants, such as polyisocyanurate, esters of isocyanuric acid or isocyanurates. Representative examples are hydroxyalkyl isocyanurates, such as tris-(2-hydroxyethyl)isocyanurate, tris(hydroxymethyl)isocyanurate, tris(3-hydroxy-n-proyl)isocyanurate or triglycidyl isocyanurate.

Nitrogen containing flame-retardants include further melamine-based flame-retardants. Representative examples are: melamine cyanurate, melamine borate, melamine phosphate, melamine pyrophosphate, melamine polyphosphate, melamine ammonium polyphosphate, melamine ammonium pyrophosphate, dimelamine phosphate, dimelamine pyrophosphate.

Further examples are: benzoguanamine, tris(hydroxyethyl) isocyanurate, allantoin, glycoluril, melamine cyanurate, melamine phosphate, dimelamine phosphate, melamine pyrophosphate, urea cyanurate, ammonium polyphosphate, a condensation product of melamine from the series melem, melam, melon and/or a higher condensed compound or a reaction product of melamine with phosphoric acid or a mixture thereof.

Representative inorganic flame retardants include, for example, aluminum trihydroxide (ATH), boehmite (AlOOH), magnesium dihydroxide (MDH), zinc borates, $CaCO_3$, layered silicates or layered double hydroxides modified with organic substituents, and mixtures thereof.

Representative organohalogen flame retardants are, for example:

Polybrominated diphenyl oxide (DE-60F, Great Lakes Corp.), decabromodiphenyl oxide (DBDPO; Saytex® 102E), tris[3-bromo-2,2-bis(bromomethyl)propyl]phosphate (PB 370®, FMC Corp.), tris(2,3-dibromopropyl)phosphate, tris (2,3-dichloropropyl)phosphate, chlorendic acid, tetrachlorophthalic acid, tetrabromophthalic acid, poly-β-chloroethyl triphosphonate mixture, tetrabromobisphenol A bis(2,3-dibromopropyl ether) (PE68), brominated epoxy resin, ethylene-bis(tetrabromophthalimide) (Saytex® BT-93), bis (hexachlorocyclopentadieno)cyclooctane (Declorane Plus®), chlorinated paraffins, octabromodiphenyl ether, hexachlorocyclopentadiene derivatives, 1,2-bis(tribromophenoxy)ethane (FF680), tetrabromo-bisphenol A (Saytex® RB100), ethylene bis-(dibromo-norbornanedicarboximide) (Saytex® BN-451), bis-(hexachlorocycloentadeno) cyclooctane, PTFE, tris-(2,3-dibromopropyl)-isocyanurate, and ethylene-bis-tetrabromophthalimide.

The organohalogen flame retardant mentioned above routinely combined with an inorganic oxide synergist. Most common for this use are zinc or antimony oxides, e.g. $Sb_2O_3$ or $Sb_2O_5$. Boron compounds are suitable, too.

The above-mentioned additional flame-retardant classes are advantageously contained in the composition of the invention in an amount from about 0.5% to about 45.0% by weight of the organic polymer substrate; for instance about 1.0% to about 40.0%; for example about 5.0% to about 35.0% by weight of the polymer or based on the total weight of the composition.

As mentioned above, the composition according to the invention may additionally contain one or more conventional additives, for example selected from pigments, dyes, plasticizers, antioxidants, thixotropic agents, levelling assistants, basic co-stabilizers, metal passivators, metal oxides, organophosphorus compounds, further light stabilizers and mixtures thereof, especially pigments, phenolic antioxidants, calcium stearate, zinc stearate, UV absorbers of the 2-hydroxy-benzophenone, 2-(2'-hydroxyphenyl)benzotriazole and/or 2-(2-hydroxyphenyl)-1,3,5-triazine groups.

Preferred additional additives for the compositions as defined above are processing stabilizers, such as the above-mentioned phosphites and phenolic antioxidants, and light stabilizers, such as benzotriazoles. Preferred specific antioxidants include octadecyl 3-(3,5-di-tert-butyl-4-hydroxyphenyl) propionate (IRGANOX 1076), pentaerythritol-tetrakis [3-(3,5-di-tert-butyl-4-hydroxyphenyl)propionate] (IRGANOX 1010), tris(3,5-di-tert-butyl-4-hydroxyphenyl) isocyanurate (IRGANOX 3114), 1,3,5-trimethyl-2,4,6-tris(3, 5-di-tert-butyl-4-hydroxybenzyl)benzene (IRGANOX 1330), triethyleneglycol-bis[3-(3-tert-butyl-4-hydroxy-5-methylphenyl)propionate] (IRGANOX 245), and N,N'-hexane-1,6-diyl-bis[3-(3,5-di-tert-butyl-4-hydroxyphenyl)-propionamide] (IRGANOX 1098). Specific processing stabilizers include tris(2,4-di-tert-butylphenyl)phosphite (IRGAFOS 168), 3,9-bis(2,4-di-tert-butylphenoxy)-2,4,8, 10-tetraoxa-3,9-diphosphaspiro[5.5]undecane (IRGAFOS 126), 2,2',2''-nitrilo[triethyl-tris(3,3',5,5'-tetra-tert-butyl-1, 1'-biphenyl-2,2'-diyl)]phosphite (IRGAFOS 12), and tetrakis (2,4-di-tert-butyl-phenyl)[1,1-biphenyl]-4,4'-diylbisphosphonite (IRGAFOS P-EPQ). Specific light stabilizers include 2-(2H-benzotriazole-2-yl)-4,6-bis(1-methyl-1-phenylethyl) phenol (TINUVIN 234), 2-(5-chloro(2H)-benzotriazole-2-yl)-4-(methyl)-6-(tert-butyl)phenol (TINUVIN 326), 2-(2H-benzotriazole-2-yl)-4-(1,1,3,3-tetramethylbutyl)phenol (TINUVIN 329), 2-(2H-benzotriazole-2-yl)-4-(tert-butyl)-6-(sec-butyl)phenol (TINUVIN 350), 2,2'-methylenebis(6-(2H-benzotriazol-2-yl)-4-(1,1,3,3-tetramethylbutyl)phenol) (TINUVIN 360), and 2-(4,6-diphenyl-1,3,5-triazin-2-yl)-5-[(hexyl)oxy]-phenol (TINUVIN 1577), 2-(2'-hydroxy-5'-methylphenyl)benzotriazole (TINUVIN P), 2-hydroxy-4-(octyloxy)benzophenone (CHIMASSORB 81), 1,3-bis-[(2'-cyano-3',3'-diphenylacryloyl)oxy]-2,2-bis-{[(2'-cyano-3',3'-diphenylacryloyl)oxy]methyl}-propane (UVINUL 3030, BASF), ethyl-2-cyano-3,3-diphenylacrylate (UVINUL 3035, BASF), and (2-ethylhexyl)-2-cyano-3,3-diphenylacrylate (UVINUL 3039, BASF).

The additives mentioned above are preferably contained in an amount of 0.01 to 10.0%, especially 0.05 to 5.0%, relative to the weight of the polymer substrate b).

The incorporation of the components defined above into the polymer component is carried out by known methods such as dry blending in the form of a powder, or wet mixing in the form of solutions, dispersions or suspensions for example in an inert solvent, water or oil. The additive components a) and b) and optional further additives may be incorporated, for example, before or after molding or also by applying the dissolved or dispersed additive or additive mixture to the polymer material, with or without subsequent evaporation of the solvent or the suspension/dispersion agent. They may be added directly into the processing apparatus (e.g. extruders, internal mixers, etc.), e.g. as a dry mixture or powder, or as a solution or dispersion or suspension or melt.

The addition of the additive components to the polymer substrate can be carried out in customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contra-rotating and co-rotating twin-screw extruders, planetary-gear extruders, ring extruders or co-kneaders. It is also possible to use processing machines provided with at least one gas removal compartment to which a vacuum can be applied.

Suitable extruders and kneaders are described, for example, in *Handbuch der Kunststoffextrusion*, Vol. 1 Grundlagen, Editors F. Hensen, W. Knappe, H. Potente, 1989, pp. 3-7, ISBN:3-446-14339-4 (Vol. 2 Extrusionsanlagen 1986, ISBN 3-446-14329-7).

For example, the screw length is 1-60 screw diameters, preferably 35-48 screw diameters. The rotational speed of the screw is preferably 10-600 rotations per minute (rpm), preferably 25-300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components is added, these can be premixed or added individually.

The additive components a) and optional further additives can also be sprayed onto the polymer substrate b). The additive mixture dilutes other additives, for example the conventional additives indicated above, or their melts so that they can be sprayed also together with these additives onto the polymer substrate. Addition by spraying during the deactivation of the polymerisation catalysts is particularly advantageous; in this case, the steam evolved may be used for deactivation of the catalyst. In the case of spherically polymerised polyolefins it may, for example, be advantageous to apply the additives of the invention, optionally together with other additives, by spraying.

The additive components a) and optional further additives can also be added to the polymer in the form of a master batch ("concentrate") which contains the components in a concentration of, for example, about 1.0% to about 40.0% and preferably 2.0% to about 20.0% by weight incorporated in a polymer. The polymer is not necessarily of identical structure than the polymer where the additives are added finally. In such operations, the polymer can be used in the form of powder, granules, solutions, and suspensions or in the form of lattices.

Incorporation can take place prior to or during the shaping operation. The materials containing the additives of the invention described herein preferably are used for the production of molded articles, for example roto-molded articles, injection molded articles, profiles and the like, and especially a fibre, spun melt non-woven, film or foam.

A preferred embodiment of the invention furthermore relates to a process for the production of an epoxy resin composition having flame retardant properties which comprises mixing at least one polyfunctional epoxide compound b), an effective amount of at least one melamine phosphonate salt (I), optionally combined with oxaphosphorinoxide or a derivative thereof, and a hardener compound, optionally in the presence of a suitable accelerator, such as methyl imidazole.

The process is carried out in a known manner by analogous methods, such as the ones described in U.S. Pat. No. 5,084,546.

According to a preferred embodiment, the invention relates to a mixture, which comprises the melamine phenylphosphonate salt of the formula (I') in combination with 6H-dibenz[c,e][1,2]-oxazaphosphorin-6-oxide of the formula (II) or a derivative thereof.

The components (I') and (II) are admixed to the polyfunctional epoxide compound in concentrations of 0.05-30.0 wt. %, preferably 0.1-20.0 wt. % for component (I') and 0.5-40.0 wt. %, preferably 1.0-25 wt. % for component (II).

The preferred ratio of components (I'):(II) is in the range 10:1-1:10, preferably 5:1-1:5.

A further embodiment of the invention relates to a process for imparting flame retardancy to a hardened polyfunctional epoxide composition, which process comprises adding the above-defined flame retardant mixture and a hardener compound to the polyfunctional epoxide.

A further embodiment of the invention relates to a process for imparting flame retardancy to a polymer substrate, which process comprises adding component a) to the polymer substrate b).

The materials containing the inventive compositions described herein are for example used for the production of molded articles, resin transfer molding, sheet molding compounds (SMC), bulk molding compounds (BMC), printed circuit boards, printed wiring boards, (pultruded) profiles, mono- and multilayer films, laminates, e.g. textile laminates, composites for planes, trains, coaches, automotive, ship, boats, construction, pipes, winded laminated (tanks), surface coatings and the like.

The following examples illustrate the invention, but are not to be construed to limit the scope thereof.

Components and Reagents Used:
Melamine: Ciba Specialty Chemicals;
Phenylphosphonic acid: Aldrich, Germany;
Bisphenol A type epoxy resin: Araldite® GT 6071, Huntsman Advanced Materials, Basel, Switzerland;
o-Cresol Novolac epoxy resin: Araldite® ECN 1280, Huntsman Advanced Materials, Basel, Switzerland;
Hardener: Dicyandiamide (DICY), accelerator: methylimidazole, both from Aldrich, Germany;
Solvents: Methoxy-2-propanol and dimethylformamide, both from Merck Eurolab, Germany;
9,10-Dihydro-9-oxa-10-phosphaphenanthrene-10-oxide (DOPO): Ukanol®GKF, Schill & Seilacher AG, Germany;
Melamine polyphosphate: Melapur® 200, Ciba Specialty Chemicals, Switzerland;
Aluminium trihydroxide (ATH): Martinal OL 104 WE, Martinswerke, Germany;
Glass cloth: Type 7628, P-D Intergals Technologies AG, Germany.

Preparation of Melamine Phenylphosphonate

A saturated hot aqueous solution of phenylphosphonic acid (800 mmol, 126 g) is added to a saturated solution of melamine (800 mmol, 101.0 g) in 90° C. hot water under vigorous stirring. After 10 min, the reaction mixture is allowed to cool slowly to room temperature (later on to 4° C.) slowly. The procedure yields 205.0 g (721 mmol, 90.2%) of the desired product as colorless crystals (needles).

Elemental analysis for $C_9H_{13}N_6O_3P$ (284.22) calcd. [%]: C, 38.31; H, 3.93; N, 29.78; O, 17.01; P, 10.98. found (%): C, 37.95; H, 4.75; N, 29.04; O 17.12; P, 12.4. Crystal structure obtained ($C_9H_{13}N_6O_3P \cdot \frac{1}{2} H_2O$).

Test Methods to Assess Flame Retardancy

UL 94 test for "*Flammability of Plastic Materials for Parts in Devices and Appliances*", 5th edition, Oct. 29, 1996. Ratings according to the UL 94 V test are compiled in the following table (time periods are indicated for one specimen):

| Rating | After flame time [sec] | Burning drips | Burn to clamp |
|---|---|---|---|
| V-0 | <10 | No | No |
| V-1 | <30 | No | No |
| V-2 | <30 | Yes | No |
| nc | <30 | | Yes |
| nc | >30 | | No | nc: no classification

Standard Procedure

A resin formulation is prepared using different amounts of Araldite® ECN 1280 resin. 9.2 parts of DICY (solution in solvent mixture of DMF and methoxy-2-propanol), 0.3 parts of methylimidazole accelerator and 60 parts methoxy-2-propanol are added to the resin composition.

After complete mixing of the above mixture in a glass jar at 70° C. and continuous stirring for a period of 30 min, the flame retardant components according to the Table below are added and mixed thoroughly with the above mentioned mixture until a homogeneous composition is obtained.

The composition is coated onto a piece of glass cloth and heated to 170° C. for about 2-5 min in a forced draft oven. The time in the forced draft oven is varied slightly from sample to sample in order to control resin flow of the final laminate. The fibre material, now in the shape of a non-tacky prepreg, is cut into 7 strips (~180×180 mm) which are stacked upon each other in a distance holder, to assure the manufacture of laminates with uniform thickness of 1.5 mm. The strips are covered with two Teflon® plates of 1 mm thickness on the upper and the lower side of the prepreg stack. The stack is placed on a hot press, and the stacked prepregs are subjected to elevated temperature and pressure according to the following general schedule:

1 minute at 170° C. with no pressure applied, 120 minutes at 170° C. with pressure of about 3 bar applied.

The resulting laminate is then removed from the press, cooled to ambient temperature, and separated from the distance holder and Teflon® plates. The laminate is cut into pieces of ~150×150 mm by cutting off the edges with varying amounts of resin, weighed, its thickness measured, and its percent resin content determined. The laminate is cut into five strips (125×13.0 mm) which are conditioned for 24 h at 23° C. and 50% relative humidity and subsequently tested in the previously mentioned UL-94 flammability test. The data obtained in this test are presented in the Table:

TABLE

| Composition | FR Additives [wt. %] | Resin [%] | UL94 Rating [1.5 mm] | Total Burning time [sec] |
|---|---|---|---|---|
| 1 | w/o | 37.2 | n.c. | 215 |
| 2 | 20% DOPO | 35.8 | V-0 | 22 |
| 3 | 10% DOPO | 37.9 | V-1 | 80 |
| 4 | 20% Melamine phenylphosphonate | 40.7 | V-1 | 62 |
| 5 | 10% Melamine phenylphosphonate + 10% DOPO | 36.3 | V-0 | 17 |
| 6 | 5.0% Melamine phenylphosphonate + 10.0% DOPO + 5.0% Melapur® 200 | 39.7 | V-0 | 12 |
| 7 | 5.0% Melamine phenylphosphonate + 5.0% DOPO + 5.0% Melapur® 200 | 40.9 | V-0 | 48 |
| 8 | 5.0% Melamine phenylphosphonate + 5.0% DOPO + 5.0% Melapur® 200 + 20.0% ATH | 42.7 | V-0 | 19 |
| 9 | 5.0% Melamine phenylphosphonate + 5.0% DOPO + 25.0% ATH | 44.6 | V-0 | 30 |

The data presented in the Table demonstrate that the resin compositions of the invention that contain melamine phosphonate in combination with DOPO exhibit excellent flame retardant properties (UL94 V-0). By addition of MELAPUR® 200 and/or ATH to the resin compositions, the concentration of the inventive flame retardant combination of melamine phenylphosphonate and DOPO can be reduced without compromising the flame retardant properties of the compositions.

The invention claimed is:

1. A composition which comprises
a) A melamine phenylphosphonate salt of formula (I')

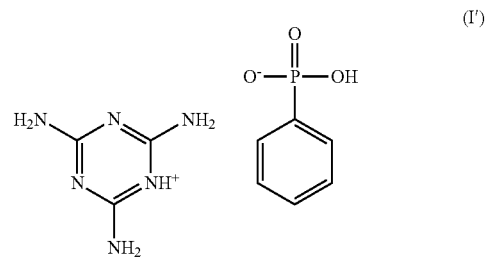 [SMILES: Nc1nc(N)[nH+]c(N)n1 ; O=P([O-])(O)c1ccccc1]

in combination with 6H-dibenz[c,e][1,2]oxaphosphorin-6-oxide (DOPO)

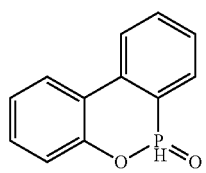

and
b) polyglycidyl ethers of o-cresol-formaldehyde and dicyandiamide hardener, where the weight:weight ratio of melamine phenylphosphonate salt to DOPO is from 1:1 to 1:2.

2. A composition according to claim 1 where the melamine phenylphosphonate salt and DOPO are each present from 5% to 10% by weight, based on the weight of the polyglycidyl ethers of o-cresol-formaldehyde.

3. A mixture, which comprises a melamine phenylphosphonate salt of formula (I')

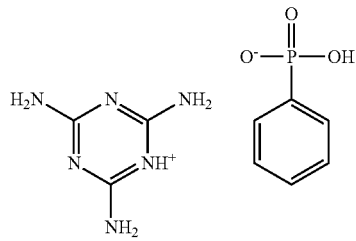

in combination with 6H-dibenz[c,e][1,2]oxaphosphorin-6-oxide (DOPO),

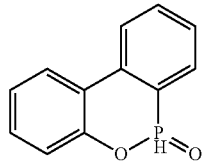

where the weight:weight ratio of the melamine phenylphosphonate salt to DOPO is from 1:1 to 1:2.

4. A process for imparting flame retardancy to a polymer substrate comprising polyglycidyl ethers of o-cresol-formaldehyde and dicyandiamide hardener, which process comprises adding thereto the mixture according to claim 3 at weight levels of from 5% to 10% by weight melamine phenylphosphonate salt and from 5% to 10% by weight DOPO, each based on the polyglycidyl ethers of o-cresol-formaldehyde.

* * * * *